US012673911B2

(12) United States Patent
Marriott

(10) Patent No.: US 12,673,911 B2
(45) Date of Patent: Jul. 7, 2026

(54) PRODUCTION OF CANNABIDIOL FROM HEMP USING SUBCRITICAL LIQUID CARBON DIOXIDE

(71) Applicant: Bridge Farm Bioscience Limited, Spalding (GB)

(72) Inventor: Ray Marriott, Kettering (GB)

(73) Assignee: Bridge Farm Bioscience Limited, Spalding (GB)

(*) Notice: Subject to any disclaimer, the term of this patent is extended or adjusted under 35 U.S.C. 154(b) by 499 days.

(21) Appl. No.: 18/253,164

(22) PCT Filed: Oct. 21, 2021

(86) PCT No.: PCT/EP2021/079275
§ 371 (c)(1),
(2) Date: May 16, 2023

(87) PCT Pub. No.: WO2022/111916
PCT Pub. Date: Jun. 2, 2022

(65) Prior Publication Data

US 2023/0416176 A1 Dec. 28, 2023

(30) Foreign Application Priority Data

Nov. 27, 2020 (EP) .................................... 20210316

(51) Int. Cl.

| | |
|---|---|
| ***C07C 37/00*** | (2006.01) |
| ***B01D 11/02*** | (2006.01) |
| ***B01D 15/40*** | (2006.01) |
| ***C07C 37/82*** | (2006.01) |
| ***C07C 39/23*** | (2006.01) |

(52) U.S. Cl.
CPC ........ *C07C 37/004* (2013.01); *B01D 11/0203* (2013.01); *B01D 11/0288* (2013.01); *B01D 15/40* (2013.01); *C07C 37/82* (2013.01); *C07C 39/23* (2013.01)

(58) Field of Classification Search
None
See application file for complete search history.

(56) References Cited

U.S. PATENT DOCUMENTS

2004/0049059 A1 3/2004 Mueller
2024/0293762 A1* 9/2024 Loft .................. B01D 11/0203

FOREIGN PATENT DOCUMENTS

WO WO 2000/025127 A1 5/2000
WO WO 2002/032420 A1 4/2002
WO WO 2013/026727 A1 2/2013

OTHER PUBLICATIONS

International Search Report and Written Opinion dated Jan. 18, 2022 for PCT Application PCT/EP2021/079275.

* cited by examiner

*Primary Examiner* — Medhanit W Bahta
(74) *Attorney, Agent, or Firm* — Daniel A. Blasiole; DeWitt LLP

(57) ABSTRACT

The present invention discloses a method for extracting cannabidiol from dried, milled and decarboxylated hemp by submitting to a subcritical liquid carbon dioxide extraction followed by a mild liquid carbon dioxide separation.

15 Claims, 7 Drawing Sheets

Figure 7
Purified product
CBD
CBDA
CBDV
Time
Signal
Full extract
THCA
THC
CBN
CBD
CBG
CBDA
CBDV
Time
Signal

PRODUCTION OF CANNABIDIOL FROM HEMP USING SUBCRITICAL LIQUID CARBON DIOXIDE

FIELD OF THE INVENTION

The present invention discloses a method for extracting cannabidiol from hemp using subcritical liquid carbon dioxide.

INTRODUCTION

It has long been known that *Cannabis* has several medicinal properties for example in the treatment of cramps, migraine, convulsions, appetite stimulation and attenuation of nausea or vomiting. Medical marijuana is also useful for glaucoma, Parkinson's disease, Huntington's disease, epilepsy and Alzheimer's disease.

Marijuana refers to varieties of *Cannabis* having a high content of Δ9-tetrahydrocannabinol (Δ9-THC), which is the psychoactive ingredient of marijuana whereas industrial hemp refers to varieties of the *Cannabis* plant having a low content of Δ9-THC.

Conventional processing of hemp and *cannabis* biomass involves multiple steps including extraction, distillation and winterisation to obtain various functional fractions from the plant material.

The extraction can be carried out by distillation which causes the CBD oil to separate from an extract of the hemp plant. The resulting CBD oil can be damaged by heating necessary for the process It can also be carried out with a solvent. Solvents can be either hydrocarbon solvents or natural solvents. Hydrocarbon solvents are inexpensive, efficient and consistent but they can leave toxic residues. Natural solvents are inexpensive, fairly efficient but they can impart a chlorophyll taste to the final product and they produce a lower concentration of CBD.

For example, WO00/25127 discloses the extraction of hemp for the isolation of tetrahydro-cannabinol from natural *cannabis* plant. It discloses an extraction process with an apolar organic solvent, followed by fractional distillation under reduced pressure.

WO2/32420 relates to a method for producing an extract containing tetrahydro-cannabinol, cannabidiol and optionally the carboxylic acids thereof from *cannabis* plant material. Said dried plant material is comminuted, then extracted with supercritical or subcritical carbon dioxide, and then separated using several separation vessels operated under different conditions. Tetrahydro-cannabinol is selectively obtained.

US2004/0049059 discloses a process for producing an extract containing tetra-hydrocannabinol, cannabidiol and the carboxylic acids thereof by first extracting the plant material under supercritical pressure and temperature conditions and then separating the extract under subcritical conditions. The disadvantage of that method is that the extraction has to be carried out on the acid forms CBDA and THCA which are much less soluble in subcritical liquid carbon dioxide than the neutral CBD and THC forms, thereby requiring very harsh extraction conditions. Such harsh conditions could damage or degrade the extracted products.

There is thus a need for a simple and safe and accurate extraction and separation process.

SUMMARY OF THE INVENTION

It is an object of the present invention to extract cannabidiol from hemp with carbon dioxide.

It is another object of the present invention to obtain purified cannabidiol.

It is also an object of the present invention to sequentially extract CBD from biomass and fractionate the extract.

It is a further object of the present invention to provide a simple and cost-effective method for extracting and purifying CBD.

It is yet another object of the present invention to prepare a CBD isolate free of cannabinoids having a tetrahydropyran ring.

The foregoing objectives have been realised as described in the independent claims. Preferred embodiments are described in the dependent claims.

LIST OF FIGURES

FIG. 1 presents the high-performance liquid chromatograms (HPLC) respectively of untreated milled biomass and of decarboxylated milled biomass.

FIG. 2 presents the HPLCs respectively of the decarboxylated milled biomass and of the subcritical extract.

Figure 6:
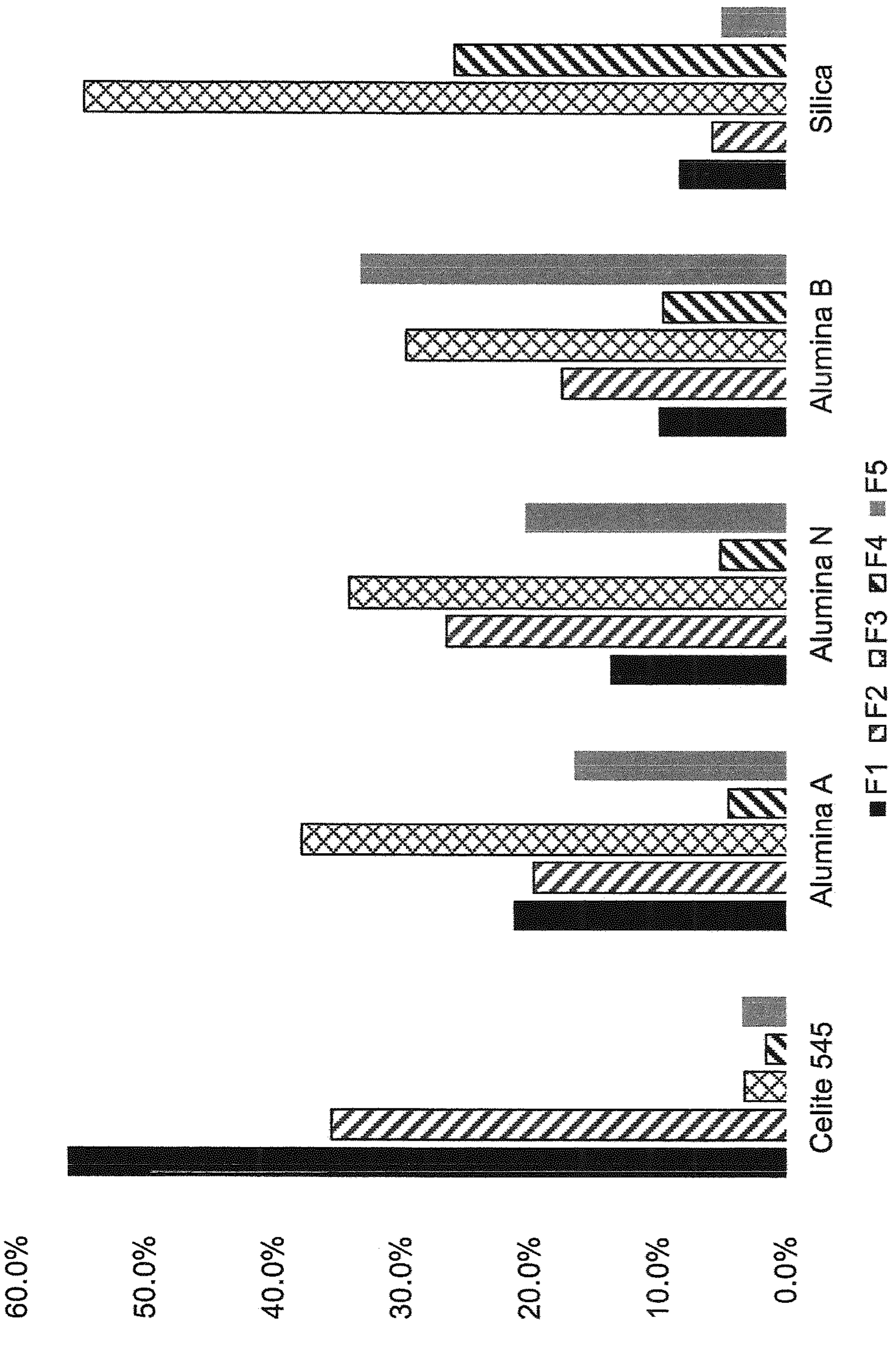

FIG. 6 represents the fraction distribution for CBD extracts in selected supports wherein F1 and F2 are the fractions obtained with subcritical carbon dioxide (85 bars/15° C.), respectively after 30 minutes and 60 minutes, F3 and F4 are the fractions obtained with supercritical carbon dioxide (300 bars/40° C.) respectively after 30 minutes and 60 minutes and F5 is the fraction obtained with supercritical carbon dioxide (300 bars/40° C.)+10% ethanol after 60 minutes.

Figure 7:

FIG. 7 represents respectively the HPLC chart showing the profile of the $CO_2$ extract obtained and purified by the method of the present invention and the HPLC chart showing the profile of the $CO_2$ extract obtained before purification on the full extract.

DETAILED DESCRIPTION OF THE INVENTION

Accordingly, the present invention discloses a method for extracting cannabidiol from hemp that comprises the steps of:

a) Providing an apparatus comprising 2 separate vessels;

b) Milling dried hemp biomass in order to obtain a product having a bulk density of at least 0.2 $g/cm^3$;

c) Decarboxylating the dried biomass of step b);

d) Filling the first vessel with the milled and decarboxylated biomass of step c)

e) Extracting a product comprising cannabidiol, tetrahydro-cannabinol Δ9-THC and Δ8-THC and other cannabinoids from the milled and decarboxylated biomass by injecting subcritical liquid carbon dioxide at a pressure of at least 65 bars and a temperature of less than 31° C., using a mass ratio carbon dioxide to biomass of at least 10 kg $CO_2$/kg biomass and for a period of time ranging between 30 minutes and 8 hours;

f) Retrieving the extraction product from step e) from the first vessel and loading it onto a support selected from celite, acidic, neutral or basic alumina or silica with a mass ratio extraction product to support ranging between 1 and 20 mass %, preferably between 5 and 10 mass %;

g) Loading the support of step f) into the second vessel:

h) Submitting the second vessel of step g), containing a support loaded with the extraction products, to a flow of subcritical liquid carbon dioxide at a mass ratio carbon dioxide to biomass of at least 10 kg $CO_2$/kg biomass and for a period of time ranging between 30 minutes and 8 hours in order to separate cannabidiol;

i) Retrieving cannabidiol;

j) Optionally continuing the separation process by submitting the second vessel to a flow of supercritical carbon dioxide at a mass ratio carbon dioxide to biomass of at least 10 kg $CO_2$/kg biomass and for a period of time ranging between 30 minutes and 8 hours in order to separate the remaining products from the support, said products comprising traces of cannabidiol, Δ9-THC and Δ8-THC, and other cannabinoids.

In another preferred embodiment according to the present invention, the extraction and separation steps are carried out sequentially in a continuous process wherein the first and second vessels are connected and the carbon dioxide is flowing from the first vessel to the second in a continuous process that comprises the steps of:

A) Providing 2 vessels connected to each other;

B) Milling dried hemp biomass in order to obtain a product having a bulk density of at least 0.2 g/cm$^3$;

C) Decarboxylating the dried biomass of step B);

D) Filling the first vessel with the milled and decarboxylated biomass of step C);

E) Filling the second vessel with a support selected from celite, acidic, neutral or basic alumina or silica:

F) In the first vessel, extracting a product comprising cannabidiol, Δ9-THC and Δ8-THC and other cannabinoids from the milled and decarboxylated biomass using subcritical liquid carbon dioxide at a pressure of at least 65 bars and a temperature of less than 31° C., with a mass ratio carbon dioxide to biomass of at least 10 kg $CO_2$/kg biomass and for a period of time ranging between 30 minutes and 8 hours;

G) Flowing the extraction product of step F) into the second vessel filled with support and submitting said second vessel to the same flow of subcritical liquid carbon dioxide using the same mass ratio carbon dioxide to biomass, the same temperature and the same pressure as in the first vessel and for a period of time ranging between 30 minutes and 8 hours;

H) Separating and retrieving cannabidiol;

I) Optionally continuing the separation process by submitting the second vessel to a flow of supercritical carbon dioxide at a mass ratio carbon dioxide to biomass of at least 10 kg $CO_2$/kg biomass and for a period of time ranging between 30 minutes and 8 hours in order to separate the remaining products from the support, said products comprising traces of cannabidiol, Δ9-THC and Δ8-THC, and other cannabinoids.

The milling of dried biomass can be carried out either with a hammer mill or with a knife mill. The hammer mill produces a coarse milled material having a bulk density of a little over 0.2 g/cm$^3$ whereas the knife mill can produce finer milled material of at least 0.3 g/cm$^3$. The choice of milling has an economical impact: coarse milled material tends to present a greater barrier to the diffusion of CO$^2$ into the biomass thereby extending the extraction time.

The milled dried hemp biomass is seen to contain a mixture of cannabidiol (CBD) and tetrahydrocannabidiol (THC) both in neutral form and acid form cannabidiolic acid (CBDA) and tertahydrocannabidiolic acid (THCA). The relative amount of those compounds varies with the nature of the starting material.

The decarboxylation step is needed in order to convert CDBA into CBD before processing takes place. The decarboxylation is carried out by heating the milled biomass to eliminate one mole of carbon dioxide as represented below

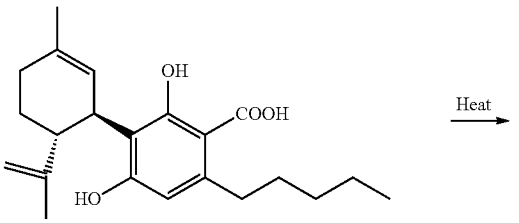

Cannabidolic acid
(Molar mass = 358.47)

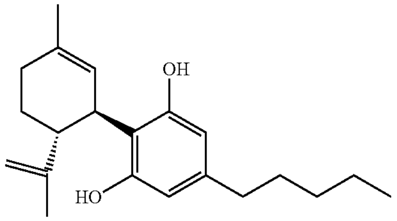

+ $CO_2$

Cannabidol
(Molar mass = 314.46)

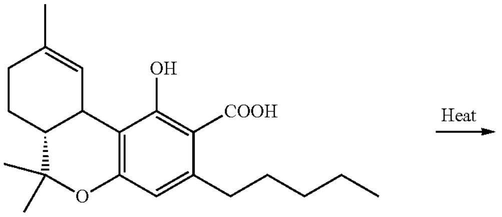

Tetrahydrocannabinolic acid
(Molar mass = 358.47)

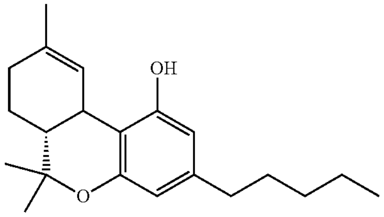

+ $CO_2$

Δ9-tetrahydrocannabinol
(Molar mass = 314.46)

Decarboxylation is a well known process which is temperature and time dependent. Several trials carried out in the present work have established that the temperature necessary for a high conversion of CDBA into CBD is of at least 100° C. for a period of time of at least 1 hour. The operating conditions cannot however be too severe and must be selected in order to minimise degradation of the final products. Preferably, the decarboxylation step is carried out at a temperature ranging between 100 and 200° C., more preferably between 110 and 130° C. Preferably it is carried out for a period of time ranging between 1 and 3 hours, more preferably between 1.5 and 2.5 hours. The decarboxylation can be carried out either in a moving bed (drum dryer/heater) or in a vacuum oven. The overall mass loss observed during the process, of less than 20 mass %, is mostly due to reduction in moisture, loss of carbon dioxide through the decarboxylation process and loss of a small amount of monoterpenes.

The decarboxylation step is an important feature of the present process. If it is not carried out before the extraction step, both the CBD and THC exist as their acid forms CBDA and THCA respectively. This means that both molecules carry one active carboxyl group which makes the present separation technique impossible. This is very different from prior art methods, such as disclosed for example in US2004/0049059 wherein the extraction step is carried out without prior decarboxylation.

The acid forms CBDA and THCA are much less soluble in subcritical liquid carbon dioxide than the neutral CBD and THC forms, thereby requiring increased pressure and temperature to carry out the extraction. In the present method, the extraction is carried out at low pressure and temperature with subcritical liquid carbon dioxide. This leaves the CBDA behind, extracting only CBD.

In addition, CBDA is much less stable than CBD, so the most stable form alone is purified in the present method.

Figure 1:
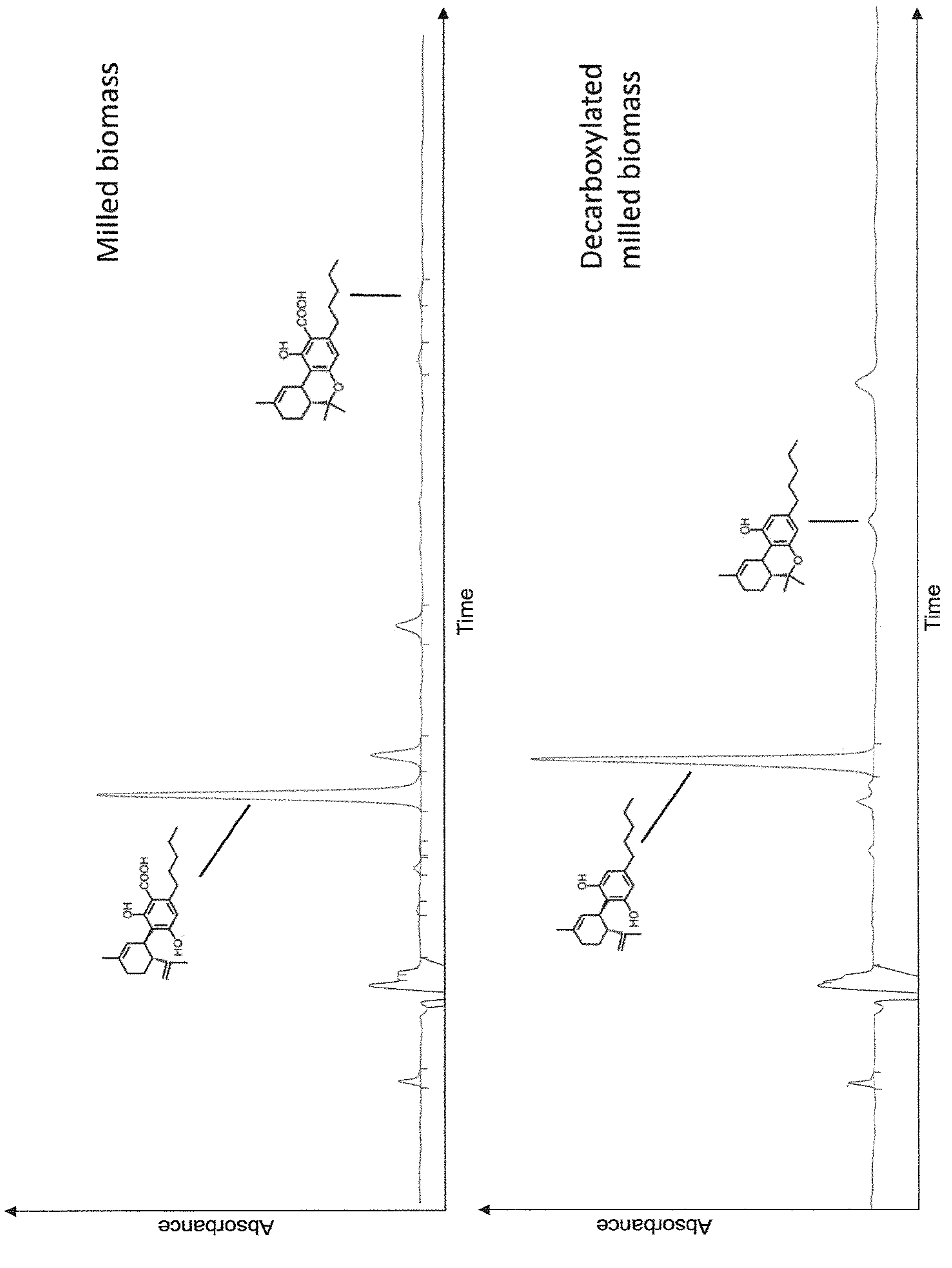

The high-performance liquid chromatograms (HPLC) of milled biomass and of decarboxylated milled biomass are presented in FIG. 1 showing clearly that the conversion of CDBA to CBD is almost complete The decarboxylated milled biomass, rich in CBD, is then submitted to the extraction step.

It is important for the subsequent extraction step to ensure that the biomass loaded into the extraction vessel has a very low moisture content and that a minimal amount of water is extracted with the CBD.

After testing several extraction conditions, it was determined that mild extraction conditions provide the best results and selectively remove the CBD, leaving behind acidic species and some THC. In the most favourable conditions, a flow of subcritical carbon dioxide is used to achieve an extraction efficiency of at least 90%. Such optimal conditions are characterised by a pressure of at least 65 bars, preferably of at least 90 bars and most preferably of at least 100 bars, and by a temperature of less than 31° C., preferably less than 25° C. and most preferably less than 20° C. The mass ratio of carbon dioxide to biomass is of at least 10 Kg $CO_2$/kg biomass, preferably at least 20 Kg $CO_2$/kg biomass and most preferably at least 25 Kg $CO_2$/kg biomass. The flow of carbon dioxide is run continually for a period of time ranging between 30 minutes and 8 hours, preferably between 1 and 6 hours.

Figure 2:
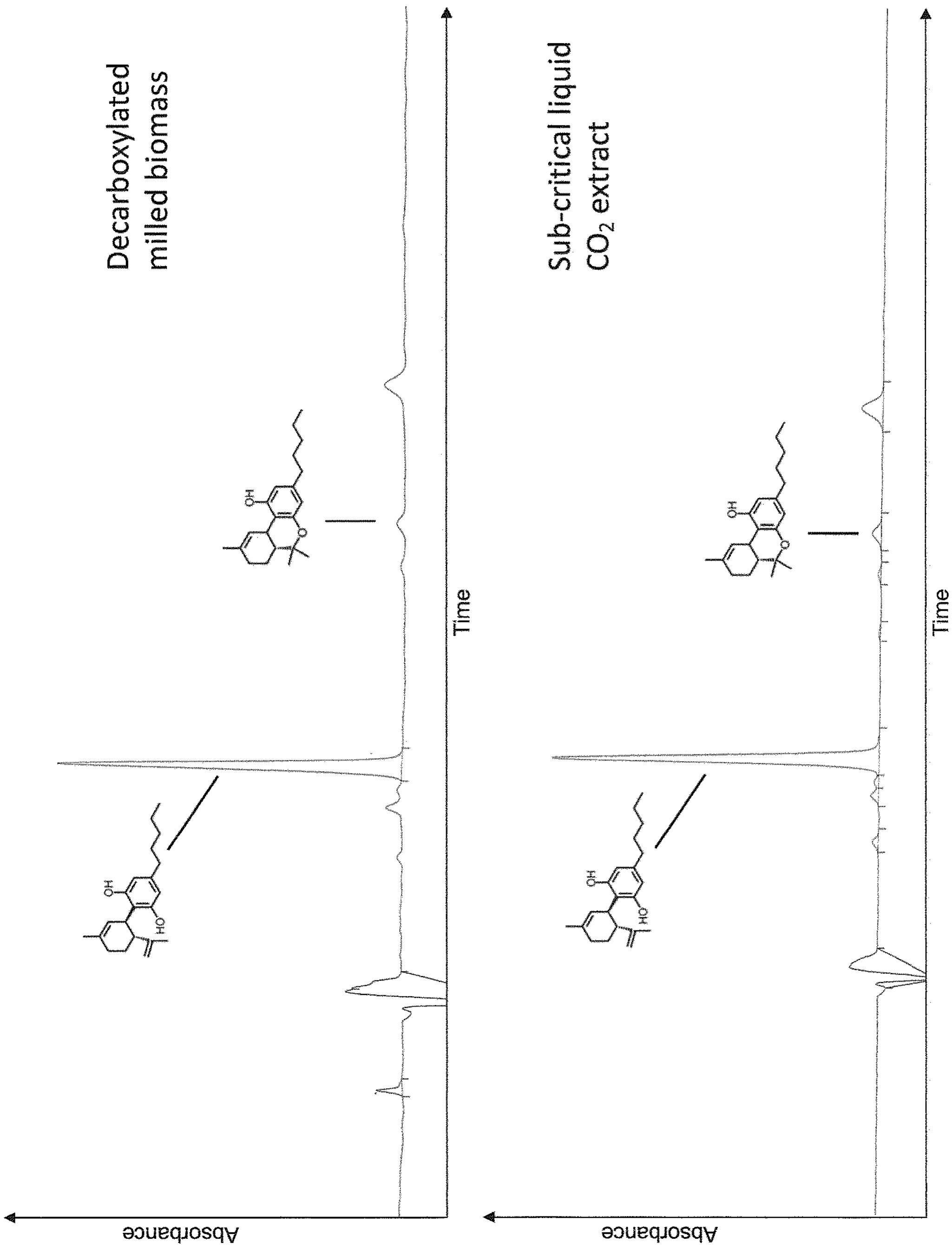

The HPLCs of the decarboxylated milled biomass and of the subcritical extract are presented in FIG. 2. The HPLC analysis of the extract clearly shows that, using the mild operating conditions of the present invention, leads to the extraction of the sole neutral cannabinoids, mainly CBD and some minor cannabinoids such as cannabidivarin (CBDV), canabigerol (CBG), Δ9-tetrahydrocannabinol (Δ9-THC), cannabichromene (CBC), cannabicyclol (CBL) or cannabinol (CBN). Acidic cannabinoids are not present in the extract. The analysis of the residue shows roughly equal amounts of CBDA and CBD confirming that the acidic form has not been extracted. The remaining components were mostly lipids from hemp seeds and low levels of waxes.

Figure 3:
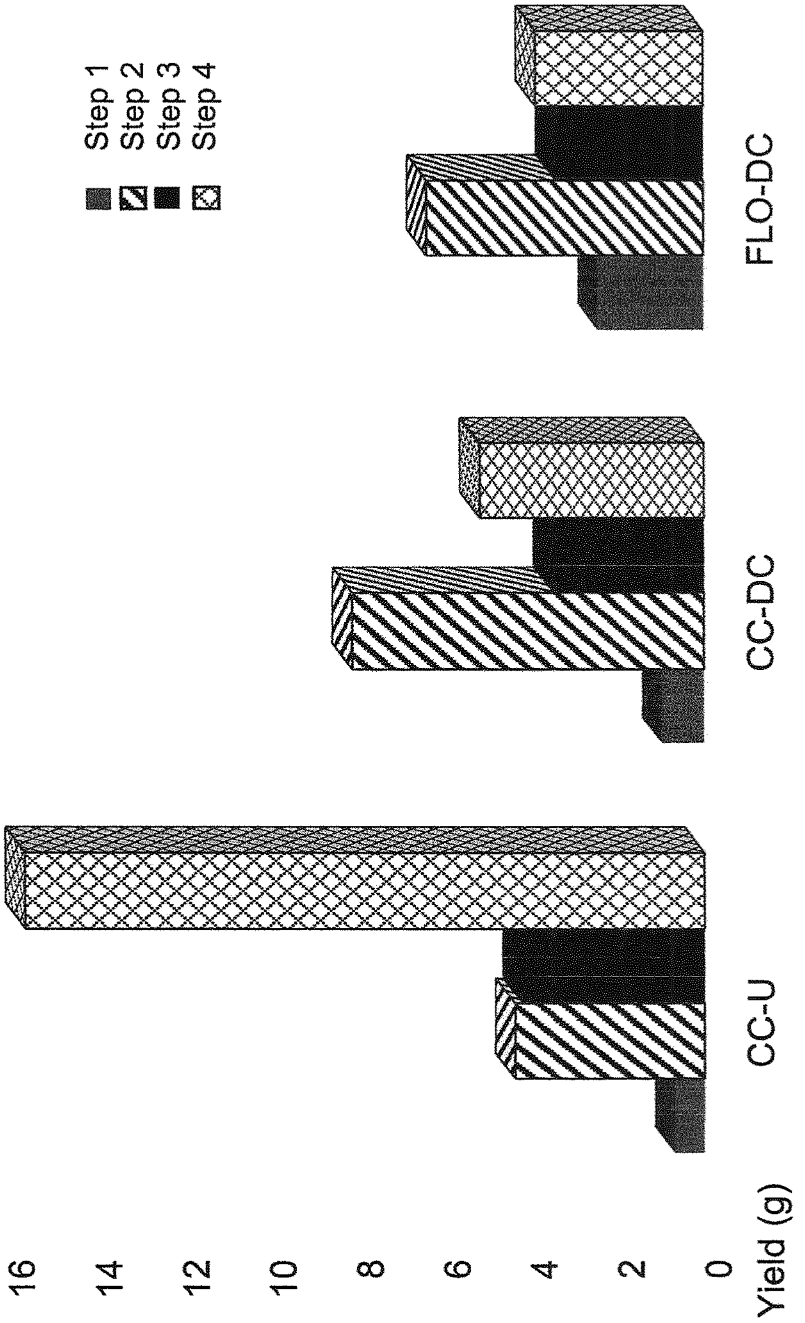
FIG. 3 represents the yields respectively of the untreated biomass (CC-U), the decarboxylated biomass of clone CC (CC-DC) and the decarboxylated biomass of clone FLO (FLO-DC) wherein the extraction is carried in 4 steps of increasing $CO_2$ density.

The extraction of the decarboxylated biomass produces a very different extraction profile from that of the untreated biomass when extracted under the same conditions, as can be seen for example in FIG. 3. In the untreated biomass (CC-U), the predominant cannabinoid is the CBDA, which because of its polarity, is extracted at the highest levels when the $CO_2$ pressure and temperature are raised. When the biomass is decarboxylated, it contains mostly CBD (CC-DC and FLO-DC), which is very soluble in $CO_2$ at low pressure and temperature, thereby producing very high yields in the early fractions. The extraction rate is however limited by diffusion through the biomass. The greater solubility of CBD in $CO_2$ is also reflected in low residual levels after extraction and wherein the residues is predominantly CBDA as can be seen in Table 1.

TABLE 1

| Residue | % m/m CBD | % m/m CBDA | Total % CBD |
|---|---|---|---|
| CC untreated | 0.056 | 1.706 | 1.553 |
| CC decarboxylated | 0.133 | 0.109 | 0.228 |
| FLO decarboxyated | 0.061 | 0.159 | 0.201 |

The overall efficiency is also considerably increased after decarboxylation and reaches values typically in excess of 97%.

Figure 4:
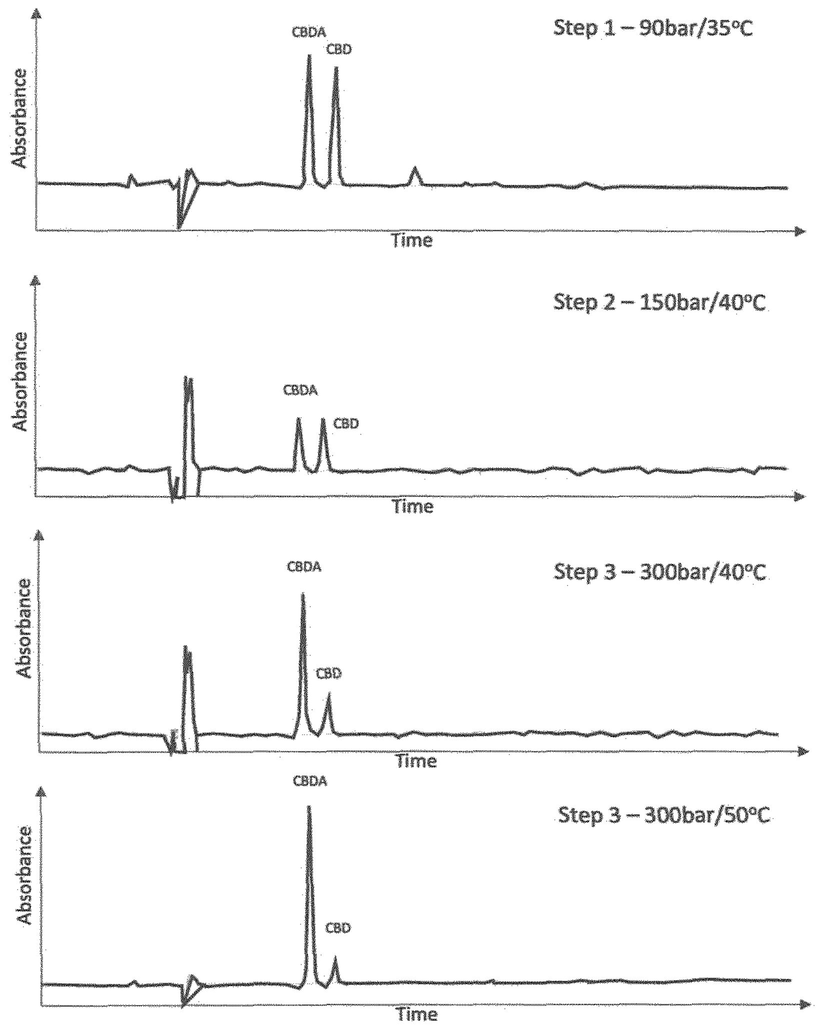
FIG. 4 represents the cannabinoid profile of extracts from untreated biomass at different conditions of temperature and pressure.
Figure 5:
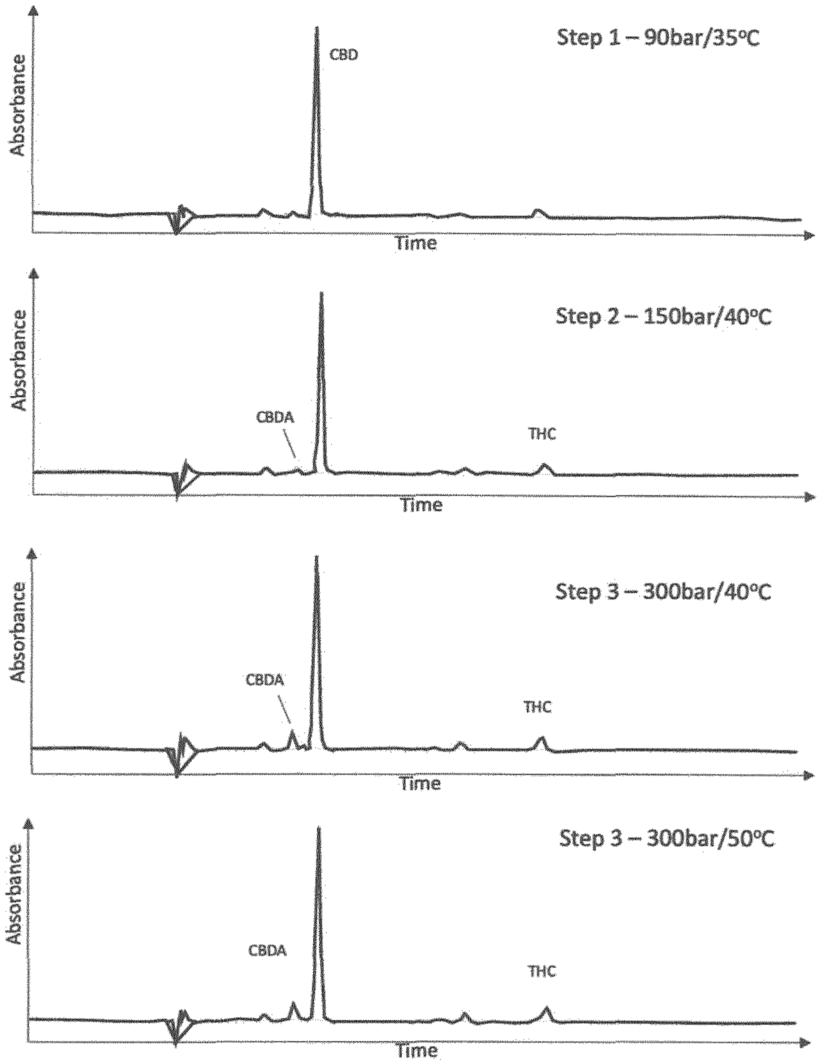
FIG. 5 represents the cannabinoid profile of extracts from decarboxylated biomass at different conditions of temperature and pressure.

HPLC analysis of the extract fractions are presented respectively in FIG. 4 for the untreated biomass and in FIG. 5 for the decarboxylated biomass. In the untreated biomass, the CBD is more soluble in low density carbon dioxide than the more polar CBDA and as the pressure and temperature are increased the ratio CBDA/CBD increases as can be seen in FIG. 4. On the contrary, the decarboxylated biomass represented in FIG. 5 shows very negligible levels of CBDA. The extraction conditions are preferably optimised to minimise wax level in order to avoid winterisation.

The extraction product is then submitted to a separation step. The product resulting from the sub-critical extraction according to the present invention contains primarily CBD and small amounts of tetrahydro Δ9-THC and Δ8-THC, and other cannabinoids. For some formulations, the THC level has to be reduced below the limit of detection. It has been disclosed in WO13/026727 that the phenols and resorcinols can be separated chromatographically using absorption onto an inert support followed by sequential elution with supercritical carbon dioxide, wherein the degree of separation is determined by the choice of support and the pressure and temperature of the supercritical carbon dioxide used in the process. The main structural difference between CBD and THC resides in the number of hydroxyl groups: 2 hydroxyl groups on the CBD molecule and one on the THC molecule. The expectation was therefore that the CBD molecule would be more strongly bound to silica or alumina inert supports and thus be removed at carbon dioxide of high polarity. Quite surprisingly, the contrary is however observed: the fractions extracted at subcritical carbon dioxide conditions such as 70 bars and 20° C. contain primarily CBD with only traces of THC, whereas the fractions extracted at supercritical carbon dioxide conditions such as 350 bars and 50° C. contain a higher proportion of THC.

The separation is carried out in the second vessel, the separation vessel, filled with support. Said second vessel can be operated as a separate unit; the support is loaded with the extraction product collected from the extraction vessel before being supplied to the second vessel.

In another preferred embodiment according to the invention, the second or purification vessel is connected to the extraction vessel and continuously collects the extracted product transferred from the extraction vessel.

The support used in the separation vessel is selected according to its ability to bind either resorcinol-type products such as CBD or phenol-type products such as THC.

The supports selected to purify the extraction products have been chosen to cover a large range of binding properties.

They can be selected from alumina having a large bulk density close to 1 g/cm$^3$ or silicas having low bulk density of the order of 0.4 g/cm$^3$.

The amount of support loaded into the vessel can vary between 40 and 100% of the vessel volume, by mass, depending upon the support selected.

The amount of loading of the extraction product onto the support is ranging between 1 and 20 mass % of extraction product to support, preferably between 5 and 10 mass %.

Celite 545 is a flux-calcined diatomaceous earth which is mostly amorphous silica. It has a packing density of 0.45 g/ml and a particle size ranging between 20 and 100 μm. It is mostly used for filtration.

Alumina is found as neutral, acidic or basic aluminium oxide. It has a packing density of 0.9 g/ml and a particle size ranging between 50 and 200 μm.

Silica is a pure silicon dioxide. It has a packing density of 0.55 g/ml and a particle size ranging between 63 and 200 μm.

Whether the separation is carried out as a separate step or continuously in a separation vessel connected to the extraction vessel, the separation vessel is packed with the selected support and the sequential fractions are retrieved using subcritical and supercritical carbon dioxide.

The object of the present invention is the production of pure cannabidiol.

Accordingly, in a preferred embodiment according to the present invention, the separation step is carried out with subcritical liquid carbon dioxide at a mass ratio carbon dioxide to biomass of at least 10 kg $CO_2$/kg biomass, at a pressure of at least 65 bars and a temperature of less than 31° C. and for a period of time ranging between 30 minutes and 8 hours, preferably between 1 and 6 hours.

Preferably, the pressure is of at least 90 bars and most preferably of at least 100 bars, and the temperature is less than 25° C. and most preferably less than 20° C. Preferably the mass ratio of carbon dioxide to biomass is of at least 20 Kg $CO_2$/kg biomass and more preferably at least 25 Kg $CO_2$/kg biomass.

The cannabidiol extracted from the support is collected and separated from the liquid carbon dioxide by depressurisation, thereby returning carbon dioxide to gas state and leaving pure cannabidiol.

Optionally, the separation step can be continued in the second vessel by submitting the support resulting from the first separation step to a flow of supercritical carbon dioxide, in order to separate further products that had remained attached to the support, comprising traces of cannabidiol, Δ9-THC and Δ8-THC, and other cannabinoids.

It can be seen from FIG. 6 that the nature of the support and the pressure and temperature of the carbon dioxide result in very different fraction distributions for CDB extracts. In FIG. 6, F1 and F2 are the fractions obtained with subcritical carbon dioxide (85 bars/15° C.), respectively after 30 minutes and 60 minutes, F3 and F4 are the fractions obtained with supercritical carbon dioxide (300 bars/40° C.) respectively after 30 minutes and 60 minutes and F5 is the fraction obtained with supercritical carbon dioxide (300 bars/40° C.)+10% ethanol after 60 minutes.

These results show that the inert support and operating conditions can be selected in order to obtain the desired cannabinoid profile.

EXAMPLES

The hemp used in this example was CC clone grown and dried in our laboratory. The dried biomass was milled using an Ecohammer 158SP mill and decarboxylated at a temperature of 115° C. for 2 hours in an OV-12 oven with a vacuum extraction after one hour for 5 minutes. Liquid $CO_2$ was obtained from BOC and the chromatographic supports from Fluorochem, and Altana. All analytical reagents were obtained from Fisher. The decarboxylated biomass had a CBD content of 5.8%.

The milled biomass was extracted in a series of trials carried out at a pressure of 110 bars and a temperature of 15° C. with a $CO_2$ flow of 40 g/min.

The results are presented in Table 2 for different supports, different amounts of carbon dioxide and different extraction times.

TABLE 2

| Run | Biomass (g) | $CO_2$ (kg) | Ratio | % CBD | % CBD post extr | | Time (hr) | Extr. % |
|---|---|---|---|---|---|---|---|---|
| 1 | 472 | 7.080 | 15 kg/kg | 5.8 | Top | 2.36 | 3 | 69.3 |
| | | | | | Bottom | 1.2 | | |
| 2 | 472 | 11.975 | 25 kg/kg | 5.8 | Top | 0.67 | 5 | 89.1 |
| | | | | | Bottom | 0.59 | | |
| 3 | 472 | 15.136 | 32 kg/kg | 5.8 | Top | 0.42 | 6 | 93.3 |
| | | | | | Bottom | 0.36 | | |

The results show that a repeatable extraction efficiency higher than 90% requires at least 25 kg $CO_2$/kg biomass, preferably at least 30 kg $CO_2$/kg biomass This was followed by the sequential fractionation of the extract. It was carried out using 2 different inert supports having different bulk densities:

- a fine silica from Fluorochem having a particle size of 30-70 μm;
- alumina UG-1 from Altana The vessel was charged according the data presented in Table 3.

TABLE 3

| | Biomass (g in 2000 ml Vessel) | Inert support (g in 500 ml vessel) | Ratio |
|---|---|---|---|
| Silica 30-70 μm (Fluorochem) | 472 | 185 | 2.55:1 |
| Alumina UG-1 (Altana) | 473 | 385 | 1.22:1 |

In each case the vessel was packed up to within 25 mm of the top and capped with cotton wool to prevent the filters blinding.

Example 1

This example was carried out using basic alumina UG-1. An amount of 473 g of biomass was extracted with 32 kg $CO_2$/kg biomass over a period of time of 5 hours at a pressure of 110 bar and a temperature of 15° C. with the extractor exit connected to the 2nd vessel containing the alumina. After a period of time of 2.5 hours the back pressure increased and the separator was found to contain a white powder. Unlike the silica, the alumina did not absorb the CBD but did bind other cannabinoids including THC resulting in a powder that had undetectable levels of THC. Further samples were taken after 4 hours and after 5 hours. These were also free of THC but had increasing levels of pigments.

After 5 hours of extraction, samples of the extracted biomass were collected from the top and bottom of the 2000 ml extractor for analysis. The $CO_2$ flow of 40 g/min was then connected to the extractor containing the alumina and run at a pressure of 300 bar and a temperature of 50° C. for a further 2 hours to collect any absorbed cannabinoids. The fraction weights and analysis are shown in Table 4.

TABLE 4

| Time (h) | Mass (g) | % CBD | % THC | CBD/THC |
|---|---|---|---|---|
| 2.5 | 18.48 | 64.79 | 0.0 | ∞ |
| 4 | 8.47 | 71.62 | 0.0 | ∞ |
| 5 | 3.43 | 66.60 | 0.0 | ∞ |
| DS-1 h | 2.65 | 52.76 | 0.92 | 57.3 |
| DS-2 h | 1.63 | 41.11 | 4.97 | 8.3 |

After 2 fractions had been collected, the vessel was depressurised and the samples of the alumina were collected from the top, middle and bottom of the vessel and analysed to yield the results shown in Table 5.

TABLE 5

| | % CBD | % THC | Ratio (CBD:THC) |
|---|---|---|---|
| Top | 2.53 | 0 | ∞ |
| Middle | 1.95 | 0 | ∞ |
| Bottom | 0 | 0 | ∞ |

These results show that undetectable levels of THC are produced with this support.

FIG. 7 represents respectively the HPLC chart showing the profile of the $CO_2$ extract obtained after separation in Example 1 and the HPLC chart showing the profile of the $CO_2$ full extract. The HPLC chart of the present purified product clearly shows that the isolate only contains CBD and is totally devoid of any other cannabinoids or controlled cannabinoids such as THC, THCA or CBN. On the contrary, the HPLC chart of the full extract, which is typically obtained by prior art methods shows the presence of other cannabinoids such as THC, THCA, CBN, CBG, CBDA and CBDV. All the cannabinoids that have a tetrahydropyran ring are legally controlled substances. It is therefore important to use a process that can efficiently and securely remove them. This is achieved in the present invention.

The invention claimed is:

1. A method for extracting cannabidiol from hemp that comprises the steps of:

a) Providing an apparatus comprising 2 separate vessels;

b) Milling dried hemp biomass in order to obtain a product having a bulk density of at least 0.2 g/$cm^3$;

c) Decarboxylating the dried biomass of step b);

d) Filling the first vessel with the milled and decarboxylated biomass of step c);

e) Extracting a product comprising cannabidiol, tetrahydro-cannabinol Δ9-THC and Δ8-THC and other cannabinoids from the milled and decarboxylated biomass by injecting subcritical liquid carbon dioxide at a pressure of at least 65 bars and a temperature of less than 31° C., using a mass ratio carbon dioxide to biomass of at least 10 kg $CO_2$/kg biomass and for a period of time ranging between 30 minutes and 8 hours;

f) Retrieving the extraction product from step e) from the first vessel and loading it onto a support selected from celite, acidic, neutral or basic alumina or silica with a mass ratio extraction product to support ranging between 1 and 20 mass %;

g) Loading the support of step f) into the second vessel;

h) Submitting the second vessel of step g), containing a support loaded with the extraction product, to a flow of subcritical liquid carbon dioxide at a mass ratio carbon dioxide to extraction product of at least 10 kg $CO_2$/kg extraction product and for a period of time ranging between 30 minutes and 8 hours in order to separate cannabidiol; and i) Separating and retrieving cannabidiol.

2. The method of claim 1 wherein the milled biomass has a density of at least 0.3 g/ml.

3. The method of claim 1 wherein the decarboxylation is carried out at a temperature of at least 100° C. for a period of time of at least 1 hour.

4. The method of claim 1 wherein the pressure for the extraction step e) is of at least 90 bars.

5. The method of claim 1 wherein the temperature in extraction step e) is of at most 25° C.

6. The method of claim 1 wherein the extraction step is carried out using subcritical carbon dioxide at a mass ratio carbon dioxide to biomass of at least 25 kg $CO_2$/kg biomass.

7. The method of claim 6 wherein the mass ratio carbon dioxide to biomass is of at least 30 kg $CO_2$/kg biomass.

8. The method of claim 1 wherein the support of step f) is selected from basic alumina in order to separate CBD with undetectable levels of THC.

9. The method of claim 1 wherein in step f), the extraction product from the first vessel is loaded onto the support with a mass ratio extraction product to support ranging between 5 and 10 mass %.

10. The method of claim 1, including the additional step of:

(j) continuing the separation process by submitting the second vessel to a flow of supercritical carbon dioxide at a mass ratio carbon dioxide to extraction product of at least 10 kg $CO_2$/kg extraction product and for a period of time ranging between 30 minutes and 8 hours in order to separate the remaining products from the support, said products comprising traces of cannabidiol, Δ9-THC and Δ8-THC, and other cannabinoids.

11. The method of claim 1 wherein the extraction and separation steps are carried out sequentially in a continuous process and wherein the extraction vessel and the separation vessel are connected to one another, which comprises the steps of:

A) Providing 2 vessels connected to each other;

B) Milling dried hemp biomass in order to obtain a product having a bulk density of at least 0.2 g/$cm^3$;

C) Decarboxylating the dried biomass of step B);

D) Filling the first vessel with the milled and decarboxylated biomass of step C);

E) Filling the second vessel with a support selected from celite, acidic, neutral or basic alumina or silica:

F) In the first vessel, extracting a product comprising cannabidiol, Δ9-THC and Δ8 -THC and other cannabinoids from the milled and decarboxylated biomass using subcritical liquid carbon dioxide at a pressure of at least 65 bars and a temperature of less than 31° C., with a mass ratio carbon dioxide to biomass of at least 10 kg $CO_2$/kg biomass and for a period of time ranging between 30 minutes and 8 hours;

G) Flowing the extraction product of step F) into the second vessel filled with support and submitting said second vessel to the same flow of subcritical liquid carbon dioxide using the same mass ratio carbon dioxide to biomass, the same temperature and the same pressure as in the first vessel and for a period of time ranging between 30 minutes and 8 hours; and H) Separating and retrieving cannabidiol.

12. The method of claim 11 wherein the pressure for the extraction step F) is of at least 90 bars.

13. The method of claim 11 wherein the temperature in extraction step F) is of at most 25° C.

14. The method of claim 11 wherein the support of step E) is selected from basic alumina in order to separate CBD with undetectable levels of THC.

15. The method of claim 11, including the additional step of:

I) continuing the separation process by submitting the second vessel to a flow of supercritical carbon dioxide at a mass ratio carbon dioxide to extraction product of at least 10 kg $CO_2$/kg extraction product and for a period of time ranging between 30 minutes and 8 hours in order to separate the remaining products from the support, said products comprising traces of cannabidiol, Δ9-THC and Δ8-THC, and other cannabinoids.

* * * * *